US011205512B2

(12) United States Patent
Shao et al.

(10) Patent No.: US 11,205,512 B2
(45) Date of Patent: Dec. 21, 2021

(54) USAGE CONTROL METHOD AND SYSTEM FOR MEDICAL DETECTION DEVICE, AND MEDICAL DETECTION DEVICE

(71) Applicant: WUXI HISKY MEDICAL TECHNOLOGIES CO., LTD., Wuxicn (CN)

(72) Inventors: Jinhua Shao, Wuxi (CN); Jin Sun, Wuxi (CN); Houli Duan, Wuxi (CN)

(73) Assignee: WUXI HISKY MEDICAL TECHNOLOGIES CO., LTD., Wuxi (CN)

( * ) Notice: Subject to any disclaimer, the term of this patent is extended or adjusted under 35 U.S.C. 154(b) by 150 days.

(21) Appl. No.: 15/652,208

(22) Filed: Jul. 17, 2017

(65) Prior Publication Data

US 2017/0316170 A1 Nov. 2, 2017

Related U.S. Application Data

(63) Continuation of application No. PCT/CN2015/081943, filed on Jun. 19, 2015.

(30) Foreign Application Priority Data

Apr. 10, 2015 (CN) .......................... 201510170707.1

(51) Int. Cl.
*G16H 40/63* (2018.01)
*G06F 21/45* (2013.01)
(Continued)

(52) U.S. Cl.
CPC ........... *G16H 40/63* (2018.01); *G06F 21/123* (2013.01); *G06F 21/34* (2013.01); *G06F 21/45* (2013.01);
(Continued)

(58) Field of Classification Search
CPC ....... G16H 40/63; G06F 21/123; G06F 21/34; G06F 21/45; G06F 21/6209; G06F 19/321
(Continued)

(56) References Cited

U.S. PATENT DOCUMENTS 5,892,838 A * 4/1999 Brady ................ G06K 9/00067
382/115
6,721,891 B1 4/2004 Borza .......................... 713/202
(Continued)

FOREIGN PATENT DOCUMENTS

| CN | 1343310 A | 4/2002 |
| CN | 101996293 A | 3/2011 |

(Continued)

OTHER PUBLICATIONS

"Elastograph" Wikipedia; (Apr. 7, 2014).
(Continued)

*Primary Examiner* — Trong H Nguyen
*Assistant Examiner* — Moeen Khan
(74) *Attorney, Agent, or Firm* — J.C. Patents

(57) ABSTRACT

A usage control method for a medical detection device, a system and a medical detection device. The method includes: receiving, by the medical detection device, an operation instruction inputted by an operator, and prompting the operator to input an authorization file when the operation instruction instructs to perform configuration authorization; receiving an authorization file inputted by the operator, and displaying an operation interface corresponding to the operation instruction when the authorization file passes authentication; where the authorization file is generated by a dongle inserted into the medical detection device according to the number of available times and the device identification; executing, by the medical detection device, con- (Continued)

figuration content inputted by the operator on the operation interface. Since the authorization file is unique to the medical detection device and an unauthorized operator cannot easily obtain the authorization file, the operation security of medical detection device can be greatly improved.

12 Claims, 3 Drawing Sheets

(51) Int. Cl.
  *G06F 21/12*   (2013.01)
  *G06F 21/34*   (2013.01)
  *G06F 21/62*   (2013.01)
  *G16H 40/60*   (2018.01)
(52) U.S. Cl.
  CPC ......... *G06F 21/6209* (2013.01); *G16H 40/60* (2018.01)
(58) Field of Classification Search
  USPC .............................................................. 726/2
  See application file for complete search history.

(56) References Cited

U.S. PATENT DOCUMENTS

| | | | |
|---|---|---|---|
| 7,032,240 B1 | 4/2006 | Gronce et al. ..................... 726/2 |
| 2004/0034304 A1* | 2/2004 | Sumi .................... A61B 5/0051 600/439 |
| 2007/0244825 A1* | 10/2007 | Semmer ................ G06F 21/123 705/59 |
| 2008/0231887 A1 | 9/2008 | Sakagami et al. ........... 358/1.15 |
| 2009/0261948 A1* | 10/2009 | Ashizawa .............. G06Q 10/06 340/10.1 |
| 2010/0058053 A1* | 3/2010 | Wood ..................... G06F 21/31 713/155 |
| 2012/0040216 A1* | 2/2012 | Parakulam ........... G05B 19/042 429/61 |
| 2013/0031981 A1* | 2/2013 | Montaldo ........... G01S 7/52036 73/606 |
| 2014/0068770 A1 | 3/2014 | Chizeck et al. ................ 726/23 |
| 2014/0258132 A1* | 9/2014 | Swamy ................ G06K 7/0004 705/67 |
| 2015/0166009 A1* | 6/2015 | Outwater ................ B60R 25/04 701/2 |
| 2015/0317899 A1* | 11/2015 | Dumbauld ......... G06Q 10/1091 340/540 |

FOREIGN PATENT DOCUMENTS

| | | |
|---|---|---|
| CN | 102054135 A | 5/2011 |
| CN | 2496144 C2 | 10/2013 |
| CN | 103401880 A | 11/2013 |
| EA | 200801582 A1 | 12/2008 |
| EP | 2 194 478 A1 | 6/2010 |
| JP | 2005-050160 A | 2/2005 |
| JP | 2011-019588 | 2/2011 |
| JP | 2011-210169 A | 10/2011 |
| JP | 2014-100270 A | 6/2014 |
| JP | 2015-023913 A | 2/2015 |
| WO | WO 2010/089304 A1 | 8/2010 |
| WO | WO 2014/009876 A2 | 1/2014 |

OTHER PUBLICATIONS

The supplementary European Search Report of corresponding European patent application No. 15888259.7-1218 / 3282383, dated Nov. 13, 2018.
The Russian Federation Examination Report of corresponding Russian patent application No. 2017138984/14(067958), dated Aug. 7, 2018.
The Australian First Examination Report of corresponding Australian patent application No. 2015390172, dated Sep. 7, 2018.
The Japanese Examination Report of corresponding Japanese patent application No. 2017-551109, dated Sep. 19, 2018.
The Chinese First Examination Report of corresponding Chinese application No. 201510170707.1, dated May 17, 2017.
The Chinese First Examination Report of corresponding Chinese application No. 201510170707.1, dated Dec. 4, 2017.
The Russian Federation Examination Report of Russian application No. 2019110514/14(020240), dated Jun. 6, 2019.
The Japanese Examination Report of corresponding Japanese application No. 2017-551109, dated Jul. 31, 2019.

* cited by examiner

USAGE CONTROL METHOD AND SYSTEM FOR MEDICAL DETECTION DEVICE, AND MEDICAL DETECTION DEVICE

CROSS-REFERENCE TO RELATED APPLICATIONS

This application is a continuation of International Application No. PCT/CN2015/081943, filed on Jun. 19, 2015, which claims priority to Chinese Patent Application No. 201510170707.1, filed on Apr. 10, 2015, entitled "USAGE CONTROL METHOD AND SYSTEM FOR MEDICAL DETECTION DEVICE, AND MEDICAL DETECTION DEVICE", both of which are hereby incorporated by reference in their entireties.

TECHNICAL FIELD

The present invention belongs to the field of data security technologies and, in particular to a usage control method for a medical detection device, a system and a medical detection device.

BACKGROUND

In recent years, the elastic imaging technology has been rapidly developed. This technology can obtain the quantitative information of the elastic distribution of viscoelastic mediums, and has very important clinical value and a broad application prospect. With the development of the elastic imaging technology, a variety of elasticity detecting devices for performing elasticity detection on viscoelastic medium such as human body are widely used. The elasticity detecting device can be separately arranged as a single medical detection device or can be integratedly arranged in a certain medical detection device in combination with other detecting devices, which are associated to some extent, in other applications.

Although the integratedly arranging is taken as an example, it is needless to say that other detecting devices that are arranged independently, such as elasticity detecting devices are also the case. The existing medical detection device is generally provided with a processor and a built-in application software in the processor. When an operator wants to perform maintenance, configuration, and other operations on the medical detection device, he needs to log into the application software, and then perform the corresponding operations after legitimacy authentication is completed.

Currently, one way to realize the operational authorization of a medical detection device is that the operator types in special instructions and enters a specific interface to carry out the relevant authorization operation.

Although the special instructions are not expressly displayed, the operator's typing in and other input operations may be easily seen and recorded by others, which thus results in security problems, and causes the developers of medical detection devices and application software to suffer from serious damage to interests.

SUMMARY

In order to overcome the problems in prior art, the present invention provides a usage control method and for a medical detection device, a system and a medical detection device. By means of the combination of the instruction input and dongle authorization, the shortcomings in the prior art that the authentication for the maintenance operation of the medical detection device by only the instruction input is likely to result in insufficient safety are overcome.

According to a first aspect of the present invention, a usage control method for a medical detection device is provided. The medical detection device includes an excitation device for generating an elastic shear wave in a viscoelastic medium and a capturing device for determining displacement data which is generated by the viscoelastic medium under action of the elastic shear wave. The medical detection device has a dongle inserted therein, and the dongle stores the number of available times and a device identification of the medical detection device. The method includes:

receiving, by the medical detection device, an operation instruction inputted by an operator, and prompting the operator to input an authorization file when the operation instruction is an instruction which instructs configuration authorization;

receiving, by the medical detection device, an authorization file inputted by the operator, and displaying an operation interface corresponding to the operation instruction when the authorization file passes authentication; in this case the authorization file is generated by the dongle according to the number of available times and the device identification;

executing, by the medical detection device, configuration content which is inputted by the operator on the operation interface.

In a first possible implementation of the first aspect, the method further includes:

receiving, by the medical detection device, a serial number and a key of the dongle inputted by the operator to bind the dongle to the medical detection device.

In a second possible implementation of the first aspect according to the first possible implementation of the first aspect, the method further includes:

receiving, by the medical detection device, a login request from the operator, obtaining the number of available times from the dongle, and obtaining the number of used times of the medical detection device from a usage log;

when the number of used times is less than or equal to the number of available times, determining, by the medical detection device, that the operator logs in successfully, so that the operator performs elasticity detection on the viscoelastic medium using the medical detection device.

In a third possible implementation of the first aspect according to the second possible implementation of the first aspect, the method further includes:

when the elasticity detection performed on the viscoelastic medium is completed by the medical detection device for one time, updating the usage log and increasing the number of used times by one, and sending a detection completion indication to the dongle, so as to enable the dongle to update the number of available times and decrease the number of available times by one according to the detection completion indication.

In a fourth possible implementation of the first aspect according to the second possible implementation of the first aspect, the method further includes:

prompting, by the medical detection device, to bind a new dongle when the number of used times is greater than the number of available times;

determining, by the medical detection device, that the operator fails to log in when there is no new dongle bound.

In a fifth possible implementation of the first aspect according to the first aspect, the first, the second, the third or the forth possible implementation of the first aspect, the device for storing the authorization file is different from the medical detection device According to a second aspect of the present invention, a usage control system for a medical detection device is provided. The medical detection device includes an excitation device for generating an elastic shear wave in a viscoelastic medium and a capturing device for determining displacement data which is generated by the viscoelastic medium under action of the elastic shear wave, the control system includes:

the medical detection device and a dongle, the dongle being connected to the medical detection device through a communication interface; the dongle storing the number of available times and a device identification of the medical detection device;

the medical detection device further includes a control module, a transceiver module, a display module and an authentication module;

the transceiver module is configured to receive an operation instruction inputted by an operator;

the control module is configured to control the display module to prompt the operator to input an authorization file when it is determined that the operation instruction is an instruction which instructs to perform configuration authorization;

the transceiver module is further configured to receive an authorization file inputted by the operator;

the authentication module is configured to authenticate the authorization file;

the control module is further configured to control the display module to display an operation interface corresponding to the operation instruction when the authorization file passed authentication; in this case the authorization file is generated by the dongle according to the number of available times and the device identification;

the control module is further configured to control the execution of configuration content which is inputted by the operator on the operation interface.

In a first possible implementation of the second aspect, the transceiver module is further configured to:

receive a serial number and a key of the dongle inputted by the operator;

the control module is further configured to bind the dongle to the medical detection device.

In a second possible implementation of the second aspect according to the first possible implementation of the second aspect, the transceiver module is further configured to:

receive a login request from the operator;

The control module is further configured to obtain the number of available times from the dongle, and obtain the number of used times of the medical detection device from a usage log;

the control module is further configured to: when the number of used times is less than or equal to the number of available times, determine that the operator logs in successfully, so that the operator performs elasticity detection on the viscoelastic medium using the medical detection device.

In a third possible implementation of the second aspect according to the second possible implementation of the second aspect, the control module is further configured to:

when the elasticity detection performed on the viscoelastic medium is completed by the medical detection device for one time, update the usage log and increase the number of used times by one, and send a detection completion indication to the dongle through the transceiver module, so as to enable the dongle to update the number of available times and decrease the number of available times by one according to the detection completion indication.

In a fourth possible implementation of the second aspect according to the second possible implementation of the second aspect, the control module is further configured to:

control the display module to prompt to bind a new dongle when the number of used times is greater than the number of available times; determine that the operator fails to log in when there is no new dongle bound.

In a fifth possible implementation of the second aspect according to the second aspect, the first, the second, the third or the forth possible implementation of the second aspect, the device for storing the authorization file is different from the medical detection device.

According to a third aspect of the present invention, a medical detection device is provided. The medical detection device has a dongle inserted therein, the dongle stores the number of available times and a device identification of the medical detection device, the medical detection device operates in the following way:

receiving, by the medical detection device, an operation instruction inputted by an operator, and prompting the operator to input an authorization file when the operation instruction is an instruction which instructs configuration authorization;

receiving, by the medical detection device, an authorization file inputted by the operator, and displaying an operation interface corresponding to the operation instruction when the authorization file passes authentication; in this case the authorization file is generated by the dongle according to the number of available times and the device identification;

executing, by the medical detection device, configuration content which is inputted by the operator on the operation interface.

The present invention provides a usage control system for a medical detection device, and a medical detection device. When the configuration authorization operation is being performed on the medical detection device, the operator enters, according to the way of the operation instruction being inputted, the prompting interface for inputting an authorization file. If the operator inputs a correct authorization file, it means that the operator has the authority to configure the medical detection device, thus the operator can perform the corresponding operation on the medical detection device. Because the authorization file is generated in advance by the dongle according to the device identification, the number of available times, and the like of the medical detection device, the authorization file is unique to the medical detection device and an unauthorized operator cannot easily obtain the authorization file, the operation security of the medical detection device can be greatly improved.

DESCRIPTION OF EMBODIMENTS

In order to make the objectives, technical solutions and advantages of the present invention more clear, the technical solutions of embodiments in the present invention will be clearly and comprehensively described below with reference to the accompanying drawings in the embodiments of the present invention. Obviously, the described embodiments are a part rather than all of the embodiments of the present invention. All other embodiments obtained by those of ordinary skill in the art based on the embodiments of the present invention without creative effort are within the protection scope of the present invention.

Figure 1:
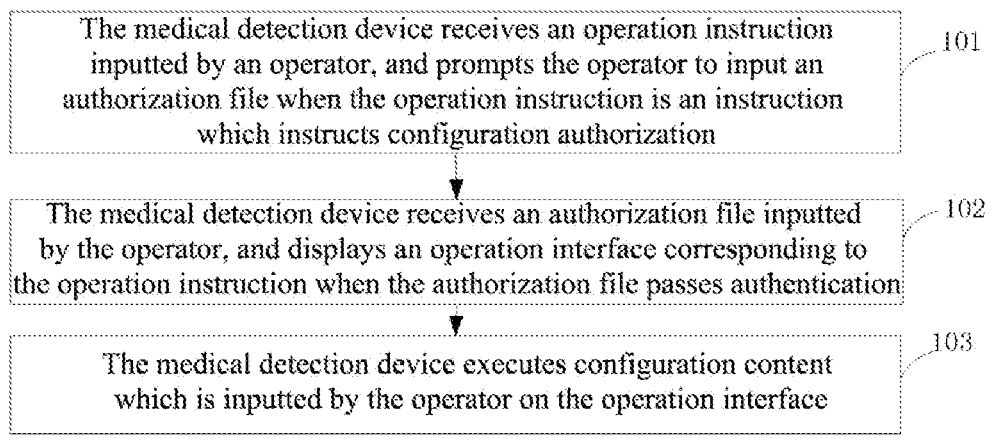
FIG. 1 is a flowchart of the first embodiment of a usage control method for a medical detection device according to the present invention.

FIG. 1 is a flowchart of the first embodiment of a usage control method for a medical detection device according to the present invention. In this embodiment, the medical detection device which is in particular an elasticity detecting device performs elasticity detection on a human body to obtain displacement data of the human body. The displacement data is obtained by performing elasticity detection on a viscoelastic medium of a detection object by the medical detection device. The medical detection device includes: an excitation device for generating an elastic shear wave in the detection object's viscoelastic medium; a capturing device for determining displacement data which is generated by the viscoelastic medium under action of the elastic shear wave. In this case the operating principles of the excitation device and the capturing device can be simply described as: on the surface of a viscoelastic organ medium such as a liver, excitation is performed by the excitation device on the viscoelastic medium to generate a shear wave, which is equivalent to generating a vibration signal, and the viscoelastic medium vibrates under the action of the vibration signal; and then the capturing device can send an ultrasonic signal to the viscoelastic medium which then generates, according to the principle of elastic mechanics, an echo response. Since the elastic stress or elastic strain of the viscoelastic organ medium is different in different states such as a normal state or a pathological state, the capturing device calculates and obtain the displacement data of the viscoelastic medium according to the echo signal before and after the press. As shown in FIG. 1, the usage control method for the medical detection device includes:

step 101, the medical detection device receives an operation instruction inputted by an operator, and prompts the operator to input an authorization file when the operation instruction is an instruction that instructs to perform configuration authorization;

step 102, the medical detection device receives an authorization file inputted by the operator, and displays an operation interface corresponding to the operation instruction when the authorization file passes authentication;

step 103, the medical detection device executes configuration content which is inputted by the operator on the operation interface.

In this embodiment, the medical detection device is connected to a dongle through a communication interface such as a USB 2.0, USB 3.0, Ethernet interface, IEEE 1394, eSATA, USB PLUS, Thunder Bolt and the like.

The dongle stores the number of available times and a device identification of the medical detection device; the dongle generates the authorization file according to the number of available times and the device identification and may be other attribute information of the medical detection device as well. The authorization file is stored in the medical detection device or in other devices that are different from the medical detection device. And the security protection for the operation of the medical detection device is realized by the dongle.

In general, the operator having authority to perform operations such as maintenance, configuration, and the like on the medical detection device is a specialized worker, rather than a person who performs elasticity detection on the viscoelastic medium of the detection object by using the medical detection device, such as a doctor. Moreover, the maintenance or configuration of the medical detection device by a specialized worker often relates to the interests of the device manufacturer or the developer of application software in the device. Therefore, in order to guarantee the above interests and to ensure the usage security of the medical detection device, it is necessary to authenticate the authority of the operator or to authorize the operator having the specific authority, so that the configuration operation is performed on the medical detection device when the operator has a corresponding authority. The configuration operation is, for example, setting some parameters for the medical detection device, performing maintenance on the medical detection device, and setting authorization for the user who can perform the elasticity detection using the medical detection device, etc.

In this embodiment, when the operator needs to perform a configuration operation on the medical detection device, the configuration authority is required. Specifically, this embodiment provides the following way of determining whether the current operator has the configuration authority:

First, the operator enters, by way of a specific operation instruction being inputted, the interface for inputting the authorization file, the operation instruction is an instruction for instructing to perform configuration authorization and can be set in advance. If the operator can input the configuration authorization instruction, it means that the operator may have the authority to configure the medical detection device.

Further, in order to finally determine whether the operator has the authority to configure the medical detection device, the operator is prompted to input the authorization file in the interface for inputting the authorization file. If the operator can input the correct authorization file, it means that the operator has the authority to configure the medical detection device. Correspondingly, if the inputted authorization file passes authentication, then the corresponding operation interface is displayed, and the operator can input relevant configuration content in the operation interface, and the medical detection device executes the configuration. In this case, the authorization file passing authentication may be, for example, that the device identification described in the authorization file is an identification of a real medical detection device, and the number of available times is a number of times subject to reasonable restrictions which does not exceed the maximum threshold.

The authorization file is generated by the dongle according to the number of currently available times of the medical detection device and the identification of the device, and may be other attribute information of the device as well, such as device position information, manufacturer information, etc. This authorization file is unique to the medical detection device so as to avoid the problem that the use of a plurality of medical detection devices by utilizing one dongle tends to cause an illegal use. In addition, the above authorization file may be stored in the medical detection device or may be stored in other devices such as a management device of the manufacturer of the medical detection device. And the storage address of the authorization file is not readily accessible to the general user, only the operator with a specialized authority is likely to access. Thus, only an operator who can input the authorization file of the medical detection device can be finally recognized as an operator having the authority to configure the medical detection device.

In this embodiment, when the authorization operation for maintenance or usage is being performed on the medical detection device, the operator enters, according to the way of the instruction being inputted, the prompting interface for inputting the authorization file. If the operator inputs the correct authorization file, it means that the operator has the authority to maintain or use the medical detection device, thus the operator can perform the corresponding operation on the medical detection device. Because the authorization file is generated in advance by the dongle according to the device identification, the number of available times, and the like of the medical detection device, the authorization file is unique to the medical detection device and an unauthorized operator, i.e., an illegal operator, cannot readily access the authorization file, the operation security of the medical detection device can be greatly improved.

Figure 2:
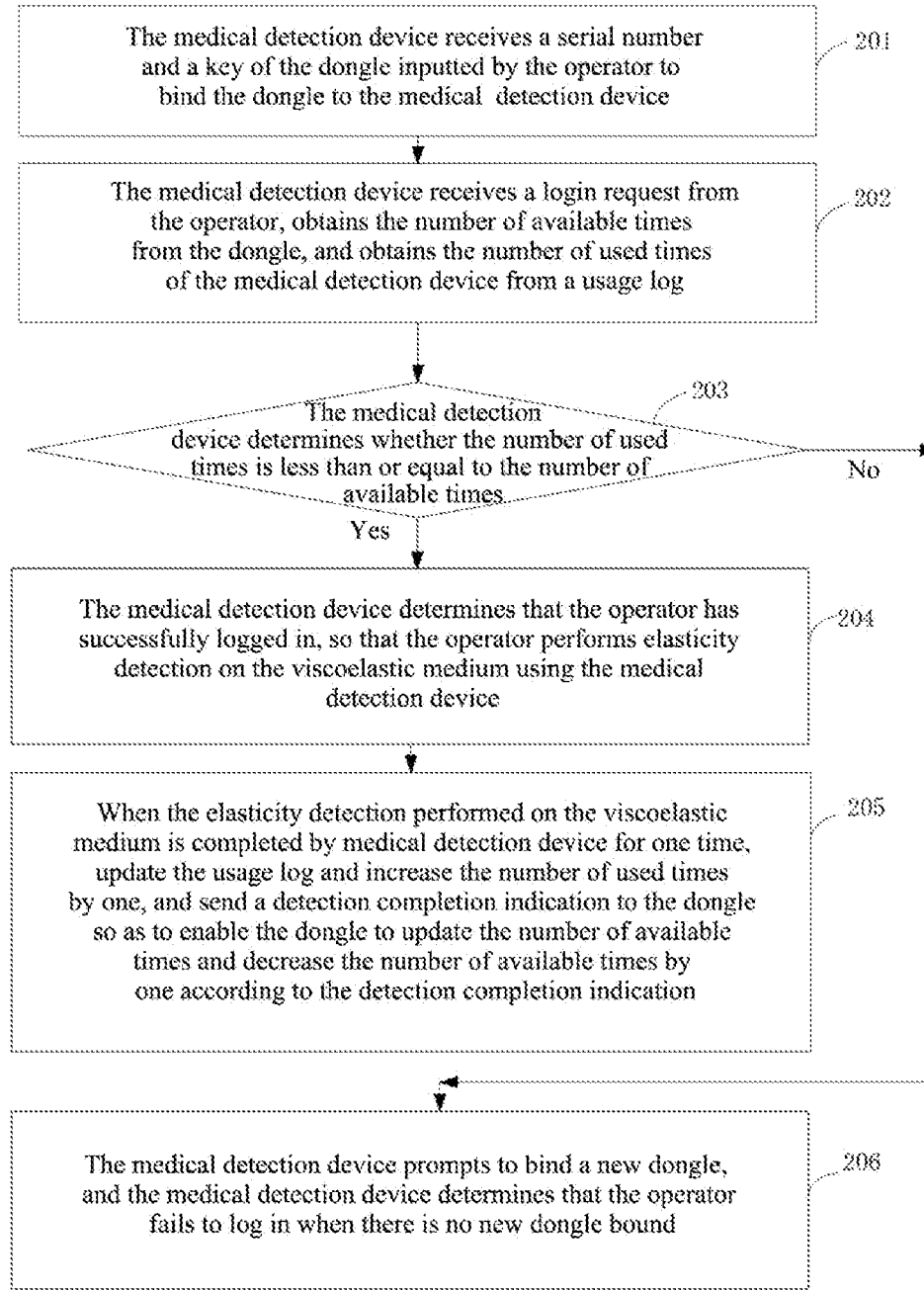
FIG. 2 is a flowchart of the second embodiment of a usage control method for a medical detection device according to the present invention.

FIG. 2 is a flowchart of the second embodiment of a usage control method for a medical detection device according to the present invention. As shown in FIG. 2, on the basis of the embodiment shown in FIG. 1, in addition to completing the configuration operation process of the medical detection device, the process of elasticity detection performed on the viscoelastic medium using the medical detection device can be achieved by the following way:

step 201, the medical detection device receives a serial number and a key of the dongle inputted by the operator, to bind the dongle to the medical detection device.

In this embodiment, the operator refers in particular to a user who performs elasticity detection on the viscoelastic medium using the medical detection device, such as a doctor.

When the operator needs to perform elasticity detection on the viscoelastic medium using the medical detection device, he first inserts the dongle and inputs the serial number and key of the dongle to bind the dongle to the medical detection device.

This is, to a certain extent, to perform authentication on the operator's identity by inputting the serial number and key of the dongle, i.e., only the operator can input the correct serial number and key, does it mean that the operator is the user who has the authority to use the medical detection device.

Step 202, the medical detection device receives a login request from the operator, obtains the number of available times from the dongle, and obtains the number of used times of the medical detection device from a usage log.

Step 203, the medical detection device determines whether the number of used times is less than or equal to the number of available times, if so, then execute steps 204 to 205, otherwise execute step 206.

Step 204, the medical detection device determines that the operator has successfully logged in, so that the operator performs elasticity detection on the viscoelastic medium using the medical detection device.

In order to be able to use the medical detection device normally for elasticity detection, the operator first needs to log into the application system. While the operator inputs the login information, the medical detection device interacts with the dongle through the communication interface, obtains the number of currently available times of the medical detection device from the dongle, and obtains the number of used times of the medical detection device from the locally stored usage log. It should be noted that if the communication between the medical detection device and the dongle is abnormal, which makes the number of the available times unable to be read, then it is determined directly that the operator fails to log in and cannot use the medical detection device.

If the number of currently used times of the medical detection device is less than or equal to the number of currently available times, then it is determined that the operator has successfully logged in and then the operator can use the medical detection device to perform elasticity detection on the viscoelastic medium.

Step 205, when the elasticity detection performed on the viscoelastic medium is completed by the medical detection device for one time, update the usage log and increase the number of used times by one, and send a detection completion indication to the dongle, so as to enable the dongle to update the number of available times and decrease the number of available times by one according to the detection completion indication.

The number of available times stored in the dongle, and the number of used times in the usage log of the medical detection device are updated in real time with the usage of the medical detection device. Specifically, when the medical detection device completes the elasticity detection for the viscoelastic medium for one time, it is necessary to update the above number of available times and the number of used times. In this case, updating the number of used times is updating the usage log to increase the number of used times by one; updating the number of available times is sending the detection completion indication to the dongle, so that the dongle updates the number of available times according to the detection completion indication to decrease the number of available times by one. In this way, the number of available times and the number of used times for the next elasticity detection performed using the medical detection device is the updated number of times.

It is worth noting that, after the operator successfully logs in, elasticity detection may be carried out for multiple times. The definition of the completion of each detection, for example, can be defined according to changes in the identity information of the detection object, or can be defined according to the completion indication inputted by the operator, or the like, and will not be limited to these.

Step 206, the medical detection device prompts to bind a new dongle, and the medical detection device determines that the operator fails to log in if there is no new dongle bound.

The medical detection device can prompt the operator to bind a new dongle if the number of used times of the medical detection device mentioned above is greater than the number of currently available times; and if there is no new dongle bound, determine that the operator fails to log in and cannot use the medical detection device to perform elasticity detection.

In this embodiment, in the process of using the medical detection device for detecting the elasticity information of the viscoelastic medium, first of all, the identity of the operator is authenticated through the binding of the dongle; then the number of currently available times of the medical detection device read from the dongle is compared with the number of used times of the medical detection device, and whether the medical detection device can be used or not is determined based on the number of available times and the number of used times, thereby achieving the authentication for using the medical detection device.

Figure 3:
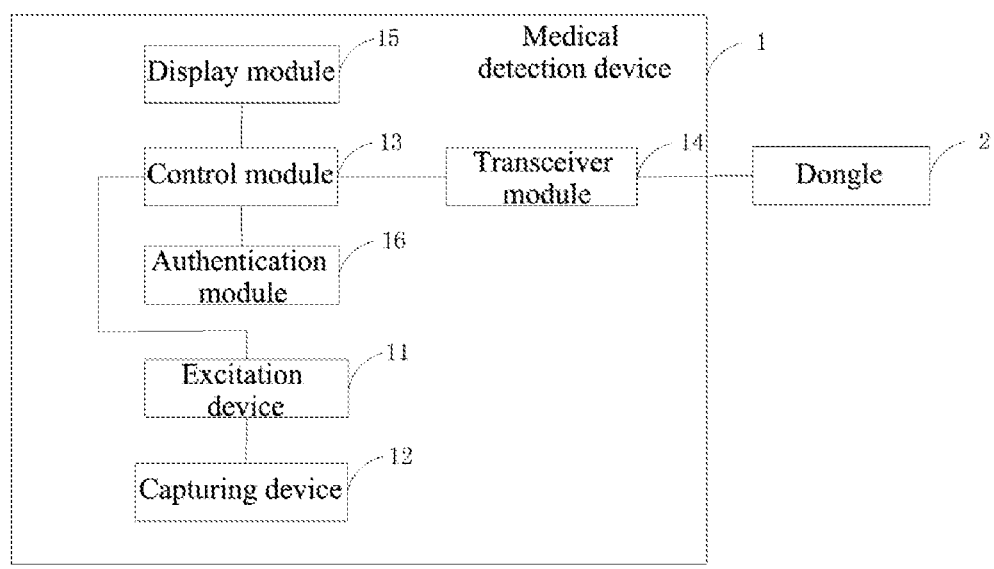
FIG. 3 is a schematic diagram of the first embodiment of a usage control system for a medical detection device according to the present invention.

FIG. 3 is a schematic diagram of the first embodiment of a usage control system for a medical detection device according to the present invention. As shown in FIG. 3, the system includes: a medical detection device 1 and a dongle 2, the dongle 2 being connected to the medical detection device 1 through a communication interface; the dongle 2 storing the number of available times and device identification of the medical detection device 1.

The medical detection device 1 includes an excitation device 11 for generating an elastic shear wave in a viscoelastic medium and a capturing device 12 for determining displacement data which is generated by the viscoelastic medium under action of the elastic shear wave.

The medical detection device 1 further includes a control module 13, a transceiver module 14, a display module 15 and an authentication module 16.

The transceiver module 14 is configured to receive an operation instruction inputted by an operator.

The control module 13 is configured to control the display module 15 to prompt the operator to input an authorization file when it is determined that the operation instruction is an instruction which instructs to perform configuration authorization.

The transceiver module 14 is further configured to receive an authorization file inputted by the operator.

The authentication module 16 is configured to authenticate the authorization file.

The control module 13 is further configured to control the display module 15 to display an operation interface corresponding to the operation instruction when the authorization file passes authentication; in this case the authorization file is generated by the dongle according to the number of available times and the device identification.

The control module 13 is further configured to control the execution of configuration content which is inputted by the operator on the operation interface.

The authorization file is stored in the medical detection device 1 or in other devices that are different from the medical detection device 1.

Further, the transceiver module 14 is also configured to receive a serial number and a key of the dongle inputted by the operator.

The control module 13 is further configured to bind the dongle 2 to the medical detection device 1.

Further, the transceiver module 14 is further configured to receive a login request from the operator.

The controlling module 13 is further configured to obtain the number of available times from the dongle 2, and obtain the number of used times of the medical detection device 1 from a usage log.

The control module 13 is further configured to: when the number of used times is less than or equal to the number of available times, determine that the operator has successfully logged in, so that the operator performs elasticity detection on the viscoelastic medium using the medical detection device.

Further, the control module 13 is further configured to: when the elasticity detection performed on the viscoelastic medium is completed by the medical detection device for one time, update the usage log and increase the number of used times by one, and send a detection completion indication to the dongle 2 through the transceiver module 14, so as to enable the dongle 2 to update the number of available times and decrease the number of available times by one according to the detection completion indication.

Further, the control module 13 is further configured to: control the display module 15 to prompt to bind a new dongle when the number of used times is greater than the number of available times; determine that the operator fails to log in when there is no new dongle bound.

It should be noted that the medical detection device in this embodiment refers particularly to an elasticity detecting device.

The control system of this embodiment can be configured to carry out the technical solutions of the method embodiments shown in FIGS. 1 and 2. The principle and technical effect are similar, and will not be repeated here.

Further, for a general variety of medical detection devices, i.e., the ones not limited to the preferences of the elasticity detecting device described above, the medical detection device has a dongle inserted therein, the dongle stores the number of available times and a device identification of the medical detection device, the medical detection device operates in the following way:

receiving, by the medical detection device, an operation instruction inputted by an operator, and prompting the operator to input an authorization file when the operation instruction is an instruction which instructs configuration authorization;

receiving, by the medical detection device, an authorization file inputted by the operator, and displaying an operation interface corresponding to the operation instruction when the authorization file passes authentication; in this case the authorization file is generated by the dongle according to the number of available times and the device identification;

executing, by the medical detection device, configuration content which is inputted by the operator on the operation interface.

In this embodiment, when the authorization operation for maintenance or usage is being performed on the medical detection device, the operator enters, according to the way of the instruction being inputted, the prompting interface for inputting the authorization file. If the operator inputs the correct authorization file, then the operator can perform a corresponding operation on the medical detection device. Because the authorization file is generated in advance by the dongle according to the device identification, the number of available times, and the like of the medical detection device, the authorization file is unique to the medical detection device and an unauthorized operator, i.e., an illegal operator, cannot readily access the authorization file, the operation security of the medical detection device can be greatly improved.

It will be appreciated by those of ordinary skill in the art that all or part of the steps for implementing the method embodiments described above may be accomplished by programming instruction related hardware. The program described above may be stored in a computer-readable storage medium which, when executed, performs the steps including the method embodiments described above; the storage medium mentioned above includes various kinds of media, such as a ROM, a RAM, a magnetic disk, or an optical disk or the like, in which program codes can be stored.

Finally, it is to be understood that the above embodiments are merely illustrative of the technical solutions of the present invention and are not to be construed to be limiting; while the present invention has been described in detail with reference to the foregoing embodiments, it will be understood by those skilled in the art that modifications may be made to the technical solutions described in the foregoing embodiments or equivalents may be substituted for some or all of the technical features therein; and such modifications or substitutions do not make the essence of the corresponding technical solutions depart from the scope of the technical solutions of the embodiments in the present invention.

What is claimed is:

1. A usage control method for an elasticity detecting device, the elasticity detecting device comprising an excitation device for generating an elastic shear wave in a viscoelastic medium and a capturing device for determining displacement data which is generated by the viscoelastic medium under action of the elastic shear wave, characterized in that, the elasticity detecting device has a dongle inserted therein, the dongle stores a quantity of available times and a device identification of the elasticity detecting device, wherein the method comprises:

receiving, by the elasticity detecting device, an operation instruction inputted by an operator, wherein the operator is a specialized worker to perform maintenance or configuration operation on the elasticity detecting device, rather than a person who performs elasticity detection on the viscoelastic medium by using the elasticity detecting device;

determining, by the elasticity detecting device, whether the operation instruction is an instruction which instructs to perform configuration authorization;

prompting, by the elasticity detecting device, the operator to input an authorization file only when the operation instruction is determined to instruct to perform configuration authorization, wherein the authorization file is unique to the elasticity detecting device and storage address of the authorization file is not obtained by an unauthorized operator;

receiving, by the elasticity detecting device, the authorization file inputted by the operator, and displaying an operation interface corresponding to the operation instruction when the authorization file passes authentication; wherein the authorization file is generated by the dongle according to the quantity of available times and the device identification;

executing, by the elasticity detecting device, configuration content which is inputted by the operator on the operation interface, wherein, the method further comprises:

receiving, by the elasticity detecting device, a serial number and a key of the dongle inputted by a user who performs elasticity detection on the viscoelastic medium using an elasticity detection device, to bind the dongle to the elasticity detecting device;

receiving, by the elasticity detecting device, a login request from the user, obtaining the quantity of available times from the dongle, and obtaining a quantity of used times of the elasticity detecting device from a usage log;

when the quantity of used times is less than the quantity of available times, determining, by the elasticity detecting device, that the user logs in successfully, so that the user performs elasticity detection on the viscoelastic medium using the elasticity detecting device;

prompting, by the elasticity detecting device, to bind a new dongle when the quantity of used times is greater than the quantity of available times; and determining, by the elasticity detecting device, that the user fails to log in when there is no new dongle bound.

2. The method according to claim 1, characterized in that, the method further comprises:

when the elasticity detection performed on the viscoelastic medium is completed by the elasticity detecting device for one time, updating the usage log and increasing the quantity of used times by one, and sending a detection completion indication to the dongle, to enable the dongle to update the quantity of available times and decrease the quantity of available times by one according to the detection completion indication.

3. The method according to claim 2, characterized in that, a device for storing the authorization file is different from the elasticity detecting device.

4. The method according to claim 1, characterized in that, a device for storing the authorization file is different from the elasticity detecting device.

5. The method according to claim 1, characterized in that, a device for storing the authorization file is different from the elasticity detecting device.

6. The method according to claim 1, characterized in that, a device for storing the authorization file is different from the elasticity detecting device.

7. The method according to claim 1, characterized in that, the method further comprises:

executing, by the elasticity detecting device, configuration content which is inputted by the operator on the operation interface to set parameters for the elasticity detecting device, perform maintenance on the-elasticity detecting device, and set authorization for user who can perform elasticity detection using the elasticity detecting device.

8. A usage control system for an elasticity detecting device, the elasticity detecting device comprising an excitation device for generating an elastic shear wave in a viscoelastic medium and a capturing device for determining displacement data which is generated by the viscoelastic medium under action of the elastic shear wave, characterized in that, the usage control system comprises:

the elasticity detecting device and a dongle, the dongle being connected to the elasticity detecting device through a communication interface; the dongle storing a quantity of available times and a device identification of the elasticity detecting device;

the elasticity detecting device further comprises: a processor and a memory storing instructions thereon, the processor when executing the instructions, being configured to:

control a transceiver to receive an operation instruction inputted by an operator, wherein the operator is a specialized worker to perform maintenance or configuration operation on the elasticity detecting device, rather than a person who performs elasticity detection on the viscoelastic medium by using the elasticity detecting device;

determine whether the operation instruction is an instruction which instructs to perform configuration authorization;

control the display module to prompt the operator to input an authorization file only when the operation instruction is determined to instruct to perform configuration authorization, wherein the authorization file is unique to the elasticity detecting device and storage address of the authorization file is not obtained by an unauthorized operator;

further control the transceiver to receive the authorization file inputted by the operator;

authenticate the authorization file;

display an operation interface corresponding to the operation instruction when the authorization file passes authentication; wherein the authorization file is generated by the dongle according to the quantity of available times and the device identification;

control execution of configuration content which is inputted by the operator on the operation interface;

the processor is further configured to:
control the transceiver to receive a serial number and a key of the dongle inputted by a user who performs elasticity detection on the viscoelastic medium using an elasticity detection device;
bind the dongle to the elasticity detecting device;
control the transceiver to receive a login request from the user;
obtain the quantity of available times from the dongle, and obtain a quantity of used times of the elasticity detecting device from a usage log;
when the quantity of used times is less than the quantity of available times, determine that login of the user is successful, so that the user performs elasticity detection on the viscoelastic medium using the elasticity detecting device; and
prompt to bind a new dongle when the quantity of used times is greater than the quantity of available times; determine that the user fails to log in when there is no new dongle bound.

9. The system according to claim 8, characterized in that, the processor is further configured to:
when the elasticity detection performed on the viscoelastic medium is completed by the elasticity detecting device for one time, update the usage log and increase the quantity of used times by one, and send a detection completion indication to the dongle through the transceiver, to enable the dongle to update the quantity of available times and decrease the quantity of available times by one according to the detection completion indication.

10. The system according to claim 8, characterized in that, a device for storing the authorization file is different from the elasticity detecting device.

11. The system according to claim 8, characterized in that, a device for storing the authorization file is different from the elasticity detecting device.

12. An elasticity detecting device, characterized in that, the elasticity detecting device has a dongle inserted therein, the dongle stores a quantity of available times and a device identification of the elasticity detecting device, the elasticity detecting device comprises a processor and a memory storing instructions thereon, and is configured to:
receive an operation instruction inputted by an operator, wherein the operator is a specialized worker to perform maintenance or configuration operation on the elasticity detecting device, rather than a person who performs elasticity detection on a viscoelastic medium by using the elasticity detecting device;
determine whether the operation instruction is an instruction which instructs to perform configuration authorization;
prompt the operator to input an authorization file only when the operation instruction is determined to instruct to perform configuration authorization, wherein the authorization file is unique to the elasticity detecting device and storage address of the authorization file is not obtained by an unauthorized operator;
receive the authorization file inputted by the operator, and displaying an operation interface corresponding to the operation instruction when the authorization file passes authentication; wherein the authorization file is generated by the dongle according to the quantity of available times and the device identification;
execute configuration content which is inputted by the operator on the operation interface; and
receive a serial number and a key of the dongle inputted by a user who performs elasticity detection on the viscoelastic medium using an elasticity detection device, to bind the dongle to the elasticity detecting device;
receive, a login request from the user, obtaining the quantity of available times from the dongle, and obtaining a quantity of used times of the elasticity detecting device from a usage log;
when the quantity of used times is less than the quantity of available times, determine that the user logs in successfully, so that the user performs elasticity detection on the viscoelastic medium using the elasticity detecting device;
prompt, to bind a new dongle when the quantity of used times is greater than the quantity of available times; and
determine, that the user fails to log in when there is no new dongle bound.

* * * * *